United States Patent [19]
Bair

[11] Patent Number: 5,865,790
[45] Date of Patent: Feb. 2, 1999

[54] METHOD AND APPARATUS FOR THERMAL PHACOEMULSIFICATION BY FLUID THROTTLING

[75] Inventor: Scott Bair, Atlanta, Ga.

[73] Assignee: SurgiJet, Inc., Irvine, Calif.

[21] Appl. No.: 755,622

[22] Filed: Nov. 25, 1996

Related U.S. Application Data

[63] Continuation-in-part of Ser. No. 578,450, Dec. 22, 1995, which is a continuation of Ser. No. 441,896, May 16, 1995, abandoned, which is a division of Ser. No. 96,297, Jul. 26, 1993, abandoned.

[51] Int. Cl.$^6$ ..................................................... A61M 1/00
[52] U.S. Cl. .............................. 604/35; 604/22; 604/295
[58] Field of Search ................................ 604/22, 35, 51, 604/294, 295, 296; 606/107, 161, 166

[56] References Cited

U.S. PATENT DOCUMENTS 5,151,084  9/1992  Khek ..................................... 606/107 X
5,322,504  6/1994  Doherty et al. ........................ 604/22 X

*Primary Examiner*—Ronald Stright, Jr.
*Assistant Examiner*—A. T. Nguyen
*Attorney, Agent, or Firm*—Harris Zimmerman

[57] ABSTRACT

A method and instrument for thermal phacoemulsification includes, in one aspect, a process for introducing high temperature water into the lens capsule of the eye for emulsification purposes. The invention provides a mechanism for heating water to the desired temperature at the point of delivery, whereby the cannula that enters the eye is maintained at a temperature sufficiently low to avoid thermal damage to surrounding eye tissue. The invention provides an isenthalpic device for delivering heated water to the lens capsule for phacoemulsification. The device includes a intraocular cannula for delivering high pressure water, and a throttling mechanism at the point of delivery for converting the energy in the water stream from pressure to heat. The throttling mechanism may comprise a capillary passage, or a porous plug, or a micro-orifice which directs the fluid stream to strike a target in the cannula bore, after which the fluid is discharged from the cannula. In a further aspect, the invention comprises a fluid pressure intensifier generating high pressure fluid pulses that are delivered through the cannula to the throttling mechanism. The use of a fluid pressure intensifier minimizes the length of tubing that must carry high pressure fluid, and the use of a throttling mechanism to heat the fluid stream assures that the tubular cannula remains within a tolerable temperature range. Moreover, the risk of a catastrophic malfunction is held to an absolute minimum.

13 Claims, 2 Drawing Sheets

METHOD AND APPARATUS FOR THERMAL PHACOEMULSIFICATION BY FLUID THROTTLING

REFERENCE TO RELATED APPLICATIONS

This patent application is a continuation-in-part of application Ser. No. 08/578,450, filed Dec. 22, 1995, which is a continuation of application Ser. No. 08/441,896, filed May 16, 1995, which is a divisional application of application Ser. No. 08/096,297, filed Jul. 26, 1993, for which priority is claimed.

BACKGROUND OF THE INVENTION

The present invention generally relates to excision and removal of tissue in surgical procedures, and more specifically to the use of fluid means for excising and removing tissue. In particular, the invention is directed toward the emulsification and removal of the lens of the eye to treat cataracts and similar disorders.

One state of the art technique for phacoemulsification involves the use of a pulsed fluid jet delivered through a small diameter cannula. An exemplary device for this purpose is disclosed in patent applications noted above and filed by the present inventor.

It has been determined that the application of hot water to a cataractus lens will more easily emulsify the lens, making it easier to aspirate the tissue through a small cannula. The optimum temperature for this purpose is in a range just below the boiling point of water. The introduction of hot water into the capsule containing the lens is a difficult and problematic task. The quantity of water must be very small, generally less than one milliliter, and well-controlled. Moreover, hot tubing or other structures for delivering heated water may damage eye tissue at any point of contact. Thus, it would seem prudent to heat the water at the point of delivery, thereby avoiding the potential for thermal damage to adjacent eye structures.

Likewise, temperature control of the heated water is critically important, particularly when operating in a temperature range that approaches the boiling point. If the water is heated at the point of delivery, the heat added to the mass of water must be proportional to the flow rate, so that a constant temperature is maintained. It is critical that this process be accurately controlled to avoid the generation of live steam at the point of delivery, which would be very damaging to the eye.

Thus, the restrictions for a heated water phacoemulsification instrument, include limited volume, constant elevated water temperature, and a cool delivery cannula. There is no device known in the prior art that is designed to emulsify and aspirate a lens using heated water, nor is there any device that is capable of meeting these stringent design criteria.

SUMMARY OF THE PRESENT INVENTION

The present invention generally comprises an instrument that is designed to emulsify and aspirate an ocular lens using high pressure, heated water. The use of heated water can produce more rapid and thorough emulsification, resulting in easier aspiration through a smaller cannula.

In one aspect, the invention comprises a process for introducing high pressure, high temperature water into the lens capsule of the eye for emulsification purposes. In particular, the invention provides means for heating the water to the desired temperature at the point of delivery, whereby the cannula that enters the eye is maintained at a temperature sufficiently low to avoid thermal damage to surrounding eye tissue.

In another aspect, the invention provides an isenthalpic device for delivering high pressure heated water to the lens capsule for phacoemulsification. The device includes a intraocular cannula for delivering high pressure water, and a throttling mechanism at the point of delivery for converting some of the energy in the water stream from pressure to heat. The throttling mechanism does no work, in a thermodynamic sense, so that the temperature increase in the water stream is approximately proportional to the drop in pressure across the throttling mechanism. The throttling mechanism may comprise a capillary passage, or a porous plug, or a micro-orifice which directs the fluid stream to strike a target in the cannula bore, after which the fluid is discharged from the cannula.

In a further aspect, the invention comprises a handpiece that is connected to a fluid source and a pneumatic source, and a surgical cannula extending from the handpiece. Within the handpiece, a fluid pressure intensifier generates high pressure fluid pulses that are delivered through the cannula. The fluid temperature is within the normal biocompatible range. At the output end of the cannula, a throttling mechanism is secured to cause a pressure drop and concomitant temperature increase in the fluid stream, whereby fluid at an elevated temperature may be discharged into a lens capsule to carry out phacoemulsification and subsequent aspiration.

The use of a fluid pressure intensifier within the handpiece minimizes the length of tubing that must carry high pressure fluid, and the use of a throttling mechanism to heat the fluid stream assures that the tubular cannula remains within a tolerable temperature range. Moreover, the risk of a catastrophic malfunction is held to an absolute minimum.

In any aspect of the invention, the temperature rise of the fluid stream at the point of delivery is determined solely by the pressure drop at the throttling mechanism. Thus the temperature of the fluid delivered to the lens capsule may be controlled with a high degree of accuracy by regulating the temperature of the fluid at the input of the device, and the pressure of the fluid arriving at the throttling mechanism.

A further aspect of the invention comprises the method for generating a high temperature fluid stream at the point of application by transmitting a fluid under high pressure through a cannula, and throttling the fluid flow at the output end of the cannula to increase the temperature of the fluid as it is discharged.

DESCRIPTION OF THE PREFERRED EMBODIMENT

The present invention generally comprises an instrument that is designed to emulsify and aspirate an ocular lens using heated water. With regard to FIG. 1, the invention includes a cannula 11 that is introduced into the lens capsule 12 of an eye 13 through a small incision 14. The cannula is adapted to deliver heated water, at a very low flow rate and volume, into the lens capsule to effect emulsification of the lens. Generally, this procedure is used to remove a cataractus lens. Thereafter, or simultaneously, the emulsified tissue may be aspirated by a vacuum cannula (not shown), that may be assembled to or separate from the cannula 11. After removal of the lens, it is a conventional practice to install a prosthetic lens that approximates the refractive power of the natural lens, whereby visual acuity may be restored to a degree that approaches, or even exceeds, visual perception prior to development of the cataract. The use of heated water may accelerate the emulsification process and result in smaller particulate size, so that aspiration is facilitated and a smaller aspiration cannula may be use.

Figure 3:
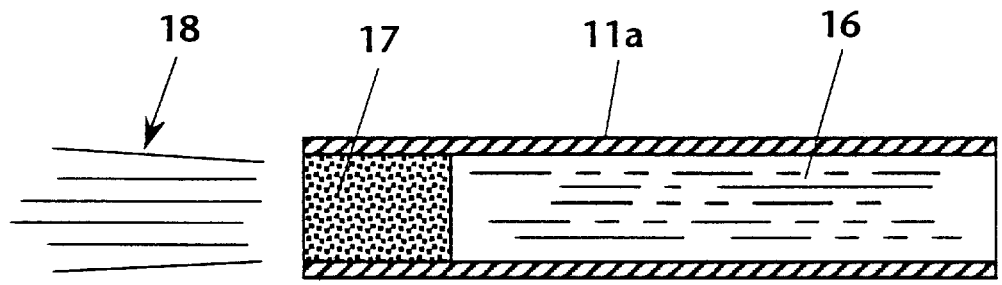
FIG. 3 is a cross-sectional view of the cannula portion of the invention, showing one embodiment of the isenthalpic throttling mechanism.

One mechanism for producing fluid at an elevated temperature is shown in FIG. 3. The intraocular cannula, here labeled 11a, includes an internal bore 16 which contains the high pressure fluid stream. A microporous throttling plug 17 is fixedly secured in the distal end of the bore 16. The plug 17 is sufficiently porous to permit the discharge of a stream 18 of fluid at elevated temperature from the distal end of the cannula. The fluid within the bore 16 is under extremely high pressure, and the plug 17 causes a significant pressure drop thereacross without doing any mechanical work. As a result, the fluid undergoes substantial heating; for water, the increase in temperature is on the order of 1° C. per 4 MPa, equivalent to 1° F. per 330 psi of pressure drop. It may be appreciated that the input pressure and the porosity of the plug create the pressure drop across the plug, which are the dominant factors in determining the temperature increase. Clearly, the temperature of the output stream 18 is the sum of the isenthalpic temperature increase at the plug 17 and the temperature of the fluid in the bore 16. Therefore, the temperature of the output stream 18 may be accurately regulated by monitoring the pressure and temperature of the fluid in the bore 16, both factors being easily controlled.

Figure 4:
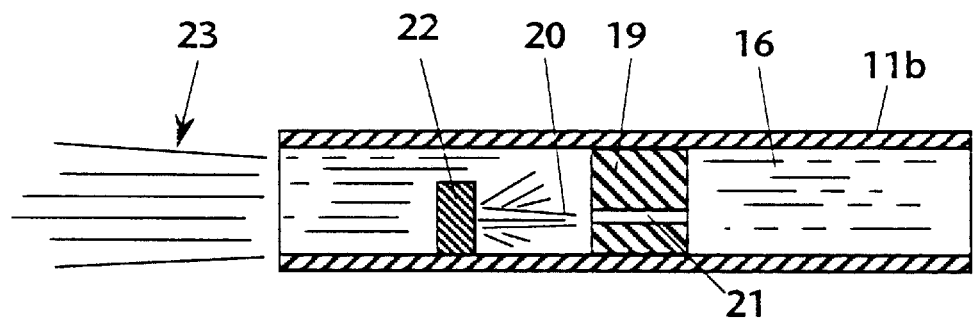
FIG. 4 is a cross-sectional view of the cannula portion of the invention, depicting a further embodiment of the isenthalpic throttling mechanism.

With regard to FIG. 4, a further embodiment of the invention involves an intraocular cannula 11b having a bore 16 which contains a high pressure fluid stream. A plug 19 is secured in the bore 16, the plug 19 including an orifice 21. A target member 22 is secured in the bore 16 downstream from the plug 19 and disposed to intercept a fluid jet 20 emanating from the orifice 21. The jet 20 impinging on the target 22 constitutes an isenthalic fluid heating mechanism. Downstream of the target 22, the cannula 11b emits an output stream 23 of high temperature fluid. As noted previously, the pressure drop at the target 22 results in a temperature rise in the fluid jet 23 emitted from the cannula, and proper regulation of the pressure and temperature of the fluid in the bore 16, together with proper selection of the size of the orifice 21, determines the output temperature and pressure of the jet 23.

Figure 5:
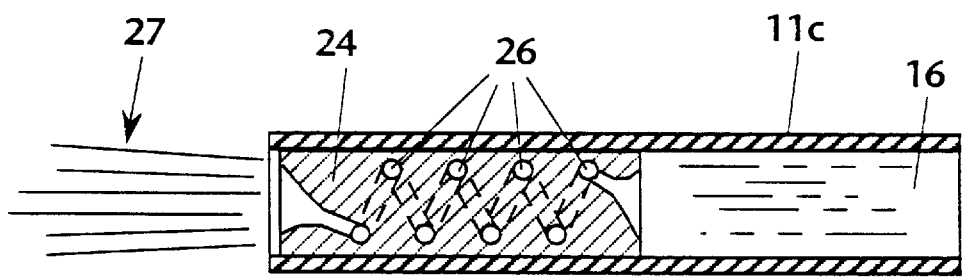
FIG. 5 is a cross-sectional view of the cannula portion of the invention, depicting another embodiment of the isenthalpic throttling mechanism.

With regard to FIG. 5, another embodiment of the mechanism for producing high pressure, heated fluid includes an intraocular cannula 11c having a bore 16 which contains a high pressure fluid stream. Secured in the distal end of the bore 16 is a plug 24. A capillary passage 26 extends tortuously through the plug 24, the passage 26 acting both as a conduit for the fluid and as an isenthalpic pressure drop. The pressure drop in the passage 26 causes conversion of some of the potential energy of the pressurized fluid to heat, resulting in a temperature increase in the output fluid jet 27. The proper choice of input temperature and pressure determines the temperature of the output 27.

It should be emphasized that in all the embodiments of FIGS. 3–5, the temperature increase imparted to the fluid stream occurs at the point of delivery to the tissue target, so that the cannula 11a–11c is not heated. Thus the risk of thermal damage to eye tissue adjacent to the lens and lens capsule is minimized. Moreover, the heating effect is invariant, whether the fluid supply is constant or pulsed.

Figure 1:
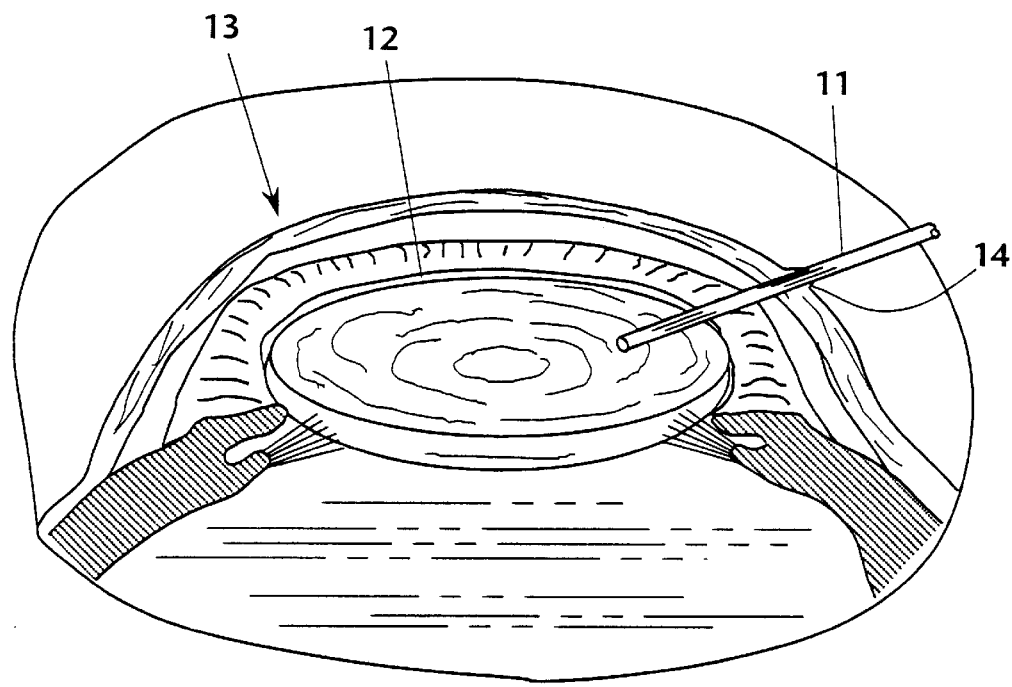
FIG. 1 is a partially cutaway perspective view of the anterior portion of an eye undergoing phacoemulsification using the present invention.
Figure 2:
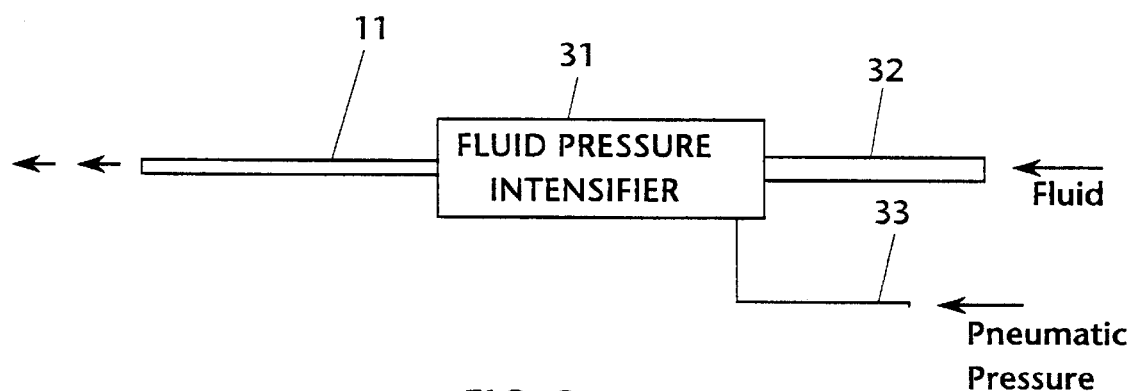
FIG. 2 is a functional block diagram of the thermal phacoemulsification device of the present invention.

With regard to FIG. 2, one embodiment of an instrument for thermal phacoemulsification includes the cannula 11 depicted in FIG. 1 and equipped as described with regard to cannula 11a–11c in any of FIGS. 3–5. The cannula is connected to the output port of a fluid pressure intensifier 31, which is described in U.S. Pat. No. 5,735,815, issued Apr. 7, 1998 to the present inventor. The fluid pressure intensifier 31 is connected through tube 32 to a source of pressurized fluid, such as water or sterile saline solution, and through hose 33 to a source of regulated pneumatic pressure. Briefly, the fluid pressure intensifier 31 operates to amplify the pressure of the input fluid, and generates extremely high pressure, low flow rate, regulated fluid pulses that are emitted as a pulsed fluid jet.

The particular advantage of the fluid pressure intensifier 31 is that extremely high pressure fluid exists only downstream of the intensifier 31; that is, within the cannula 11. There is no opportunity for a failure mode that may result in errant release of very high pressure fluid in the surgical procedure, thus minimizing the risk to the patient and attendant medical personnel.

The invention also encompasses the method for generating a high temperature fluid stream at the point of application, for phacoemulsification or other purposes. The method includes the steps of providing a high pressure fluid at the input end of a cannula, and providing a throttling mechanism at the output end of the cannula, whereby the fluid is heated as it is discharged. The increase in fluid temperature is equal to 1° F. per 330 psi of pressure drop. A clear advantage of the method of the invention is that the cannula operates at a cool temperature, eliminating the risk of thermal damage to tissue subject to incidental contact therewith, while the cannula may deliver a higher temperature fluid discharge stream to accomplish medical procedures such as thermophacoemulsification.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

I claim:

1. An instrument for thermal phacoemulsification, including:
   a cannula adapted to be introduced into an anterior portion of an eye, said cannula including an output end adapted to be introduced into a lens capsule of the eye;
   means for supplying a fluid under high pressure to said cannula to cause a fluid stream to be emitted from said output end of said cannula; and,
   means adjacent to said output end of said cannula for raising the temperature of said fluid, wherein said mean for raising the temperature includes throttling means for causing a pressure drop in said cannula and isenthalpic heating of said fluid.

2. The instrument of claim 1, wherein said throttling means includes a capillary passage formed in said cannula, said capillary passage forming a constricted flow path through said cannula.

3. The instrument of claim 1, wherein said throttling means includes a porous plug secured in said cannula, said fluid passing through said porous plug.

4. The instrument of claim 1, wherein said throttling means includes a an orifice disposed in said cannula and adapted to emit an orifice jet, and a target member secured in said cannula and disposed to intercept said orifice jet.

5. The instrument of claim 1, wherein said means for supplying a fluid comprises a fluid pressure intensifier connected to an input end of said cannula.

6. The instrument of claim 5, wherein said fluid pressure intensifier is secured within a handpiece.

7. The instrument of claim 5, wherein said fluid pressure intensifier is adapted to generate pulses of high pressure fluid.

8. A method for generating an elevated temperature fluid discharge for medical purposes, comprising the steps of:

provideing a cannula adapted to operate at a cool temperature;

supplying a high pressure, cool fluid to an input end of the cannula;

throttling the fluid flow at an output end of the cannula to convert fluid pressure into a temperature increase in the fluid, whereby the cannula emits a fluid stream from the output end that is substantially higher than the temperature of the fluid at the input end.

9. The method of claim 8, wherein said cannula emits a fluid stream from the output end that is substantially higher that the operating temperature of the cannula.

10. The method of claim 8, wherein said throttling step includes providing a microporous throttling plug at the output end of the cannula.

11. The method of claim 8, wherein said throttling step includes providing a plug at the output end of the cannula, the plug having an orifice formed therein, and a target member downstream from the orifice to intercept a fluid jet emanating from the orifice.

12. The method of claim 8, wherein said throttling step includes providing a plug at the output end of the cannula, the plug having a capillary passage extending therethrough to serve as a fluid conduit and isenthalpic pressure drop.

13. The method of claim 8, wherein the step of supplying a high pressure, cool fluid includes coupling the output of a fluid pressure intensifier to the input end of the cannula.

* * * * *